United States Patent [19]

Piccardi et al.

[11] 4,000,312

[45] Dec. 28, 1976

[54] INSECTICIDES CONTAINING AN UNSATURATED ALIPHATIC CHAIN AND PROCESS FOR PREPARING THE SAME

[75] Inventors: Paolo Piccardi; Angelo Longoni; Francesco Corda; Ciro Preziuso, all of Milan, Italy

[73] Assignee: Montedison Fibre S.p.A., Milan, Italy

[22] Filed: Jan. 10, 1975

[21] Appl. No.: 540,167

[30] Foreign Application Priority Data

Jan. 11, 1974 Italy ................................ 19332/74
Oct. 18, 1974 Italy ................................ 28583/74

[52] U.S. Cl. ...................... 424/282; 260/340.5; 260/404; 260/455 B; 260/455 R; 260/465 F; 260/473 R; 260/486 H; 260/583 G; 260/592; 260/593 H; 260/609 E; 260/609 F; 260/612 D; 260/614 R; 260/615 R

[51] Int. Cl.$^2$ ................................ C07D 317/48
[58] Field of Search ............ 260/340.5 R; 424/282

[56] References Cited

OTHER PUBLICATIONS

Chem. Abstracts–78:84553d.

Primary Examiner—Ethel G. Love

[57] ABSTRACT

Compounds consisting of a variously substituted unsaturated aliphatic chain and a terminal vinyl dichloro or trichloro substituted residue are disclosed, as well as a process for preparing them. The compounds are insecticides which exhibit an activity similar to that of the juvenile hormone and inhibit the development and metamorphosis of various insects.

7 Claims, No Drawings

INSECTICIDES CONTAINING AN UNSATURATED ALIPHATIC CHAIN AND PROCESS FOR PREPARING THE SAME

THE PRIOR ART

The controlling effect on the metamorphosis of the silkworm of the juvenile hormone, 10-epoxy-7-ethyl-3, 11-dimethyl 2,6-methyltridecadienoate, was described by Roller et al in 1967 (Anderwandte Chemie Intern. Ed. 6, 1967. pp. 179 et seq.).

Since then, considerable effort has been expended in studying the chemical structure and biological activity of analogs of that hormone, with the aim of finding simple substances easily synthesized and useful in combatting noxious insects. In fact, by hindering the development of the insects from the larvae phase to the adult state, it is possible to control infestation by insects which are harmful to people, animals and plants.

The hormone of Roller et al and its analogs have in addition to effectiveness against insects, the advantage of low toxicity

THE PRESENT INVENTION

One object of this invention is to provide a new class of compounds which have an activity similar to that of the Roller et al. juvenile hormone and are effective against a wide range of noxious insects.

Another object is to provide methods for synthesizing the new compounds.

These and other objects are achieved by the present invention which provides new class of insecticides

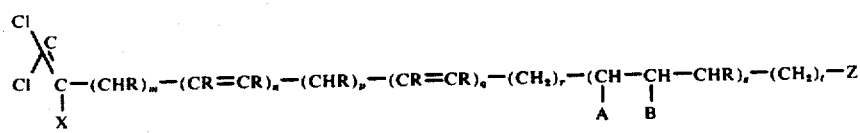

which consist of an unsaturated aliphatic chain that can be variously substituted, had dichloro- or trichlorovinyl terminal groups, and corresponds to the general formula:

in which:
X is H or Cl;
$m$, $n$, $p$, $q$, $r$, $s$ and $t$ are integers from 0 to 2;
the Rs, which may be the same or different, are H or lower alkyl radicals which may be branched and/or substituted;
A and B are H or A + B represents another bond;
Z is $-OR^1$; $-SR^1$; $-SOR^1$;

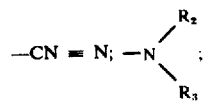

or $-COY$, in which
$R^1$ is a lower alkyl or alkenyl radical which can be branched and/or substituted; the group $-C_6H_4W\mu$ in which $\mu$ is an integer from 1 to 3 and W is H, halogen, a lower alkyl radical which can be the same as $R^1$, an alkoxy, thioalkyl, carbalkyl carboxyalkyl radical, the group $-NO_2$, the phenyl radical, a heterocyclic nucleus which can be condensed on the benzoic ring in 3,4-position; or an amine group that can be substituted by substituents which form an open chain or a cyclic chain with nitrogen;
$R^2$ and $R^3$, which can be the same or different, are H or lower alkyl radicals, optionally substituted, or $R^2$ or $R^3$ form; with nitrogen and/or other hetero atoms, a cycle of 5, 6 or 7 atoms; and
Y is H, a lower alkyl radical, a lower alkoxy radical, a cycloalkyl radical, an aryl radical, the $-OH$ group, or the group $-O-$ metal.

Presently preferred compounds within the scope of this invention are those having the general formula:

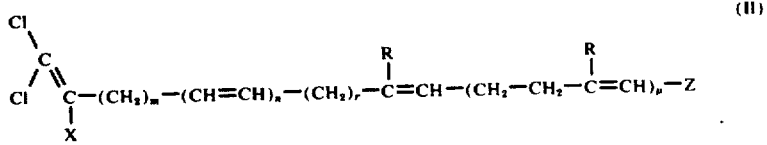

in which R, X, Z, $m$, $n$, $r$ and $p$ have the same meaning as in formula I.

The compounds of the invention are prepared by reactions which are known in general but which, so far as known, have not been applied to the preparation of products of formula I or intermediates for the production thereof.

(1) Scheme A:

-continued

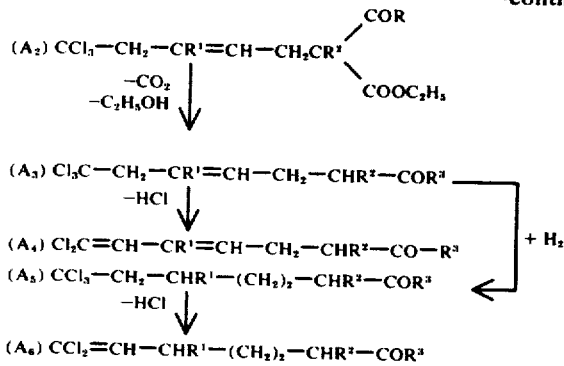

The two radicals:

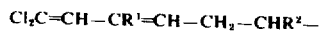

and

will be referred to hereinafter as A$^1$ and A$^2$.

Ketones similar to those obtained according to Scheme A can also be obtained according to the following Scheme B:

The two radicals:

will be designated hereinafter as, respectively, B$^3$ and B$^4$.

The reactions necessary for lengthening the chain are of the same type and common to the ketones containing radicals A$^1$, A$^2$, B$^3$ and B$^4$, hereinafter generically designated by the symbol A.

These reactions occur according to the following schemes:

(2) Scheme B:

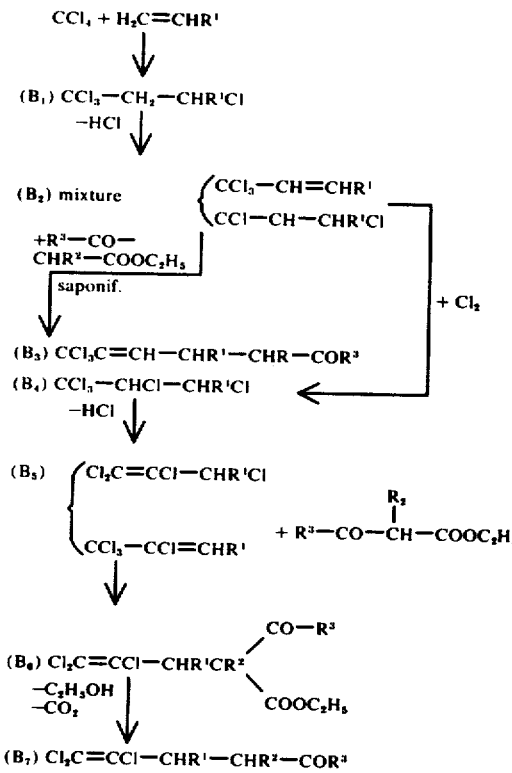

(3) Scheme C:

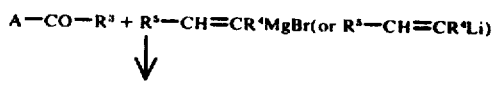

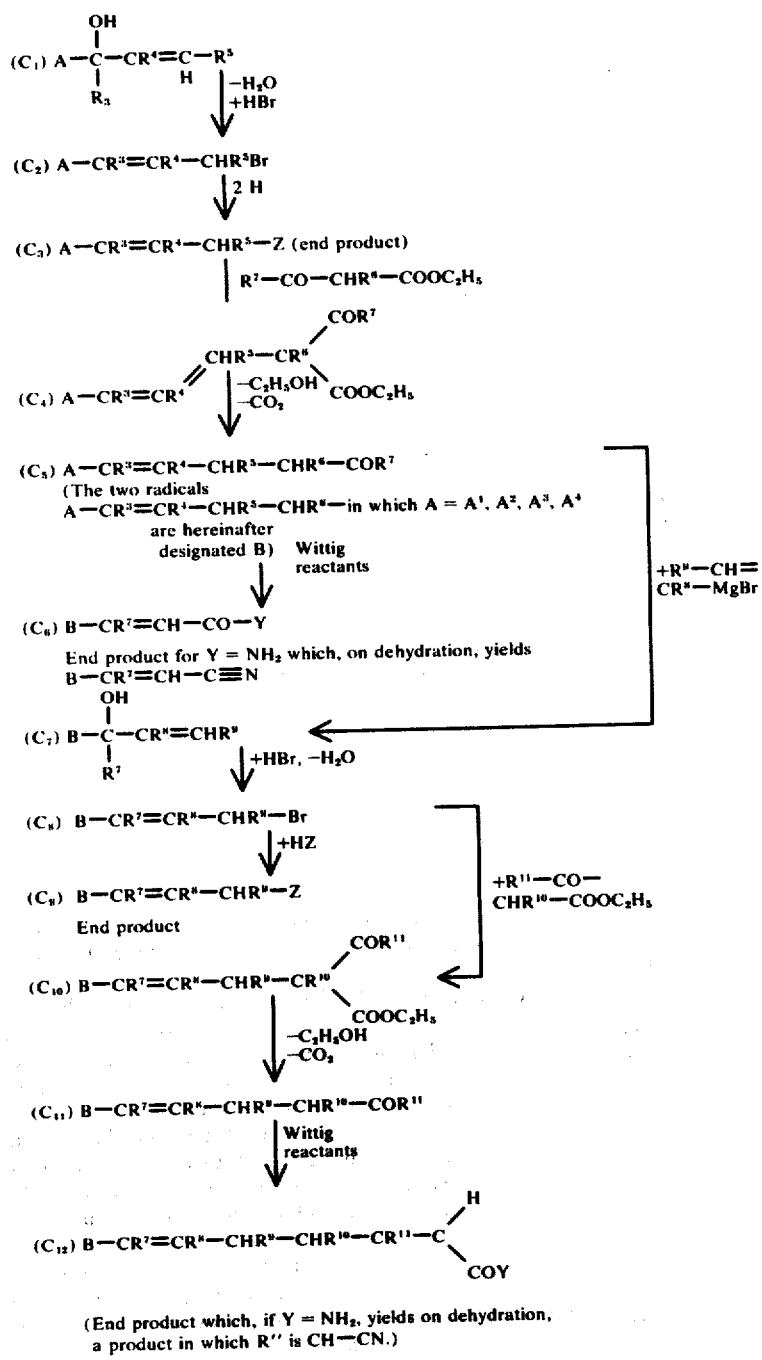
(4) Scheme D:
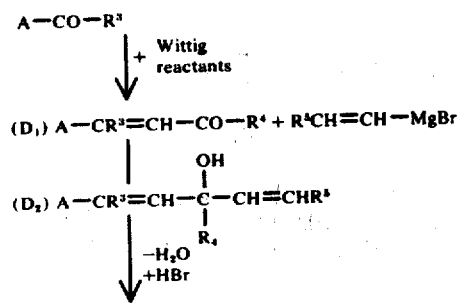

-continued

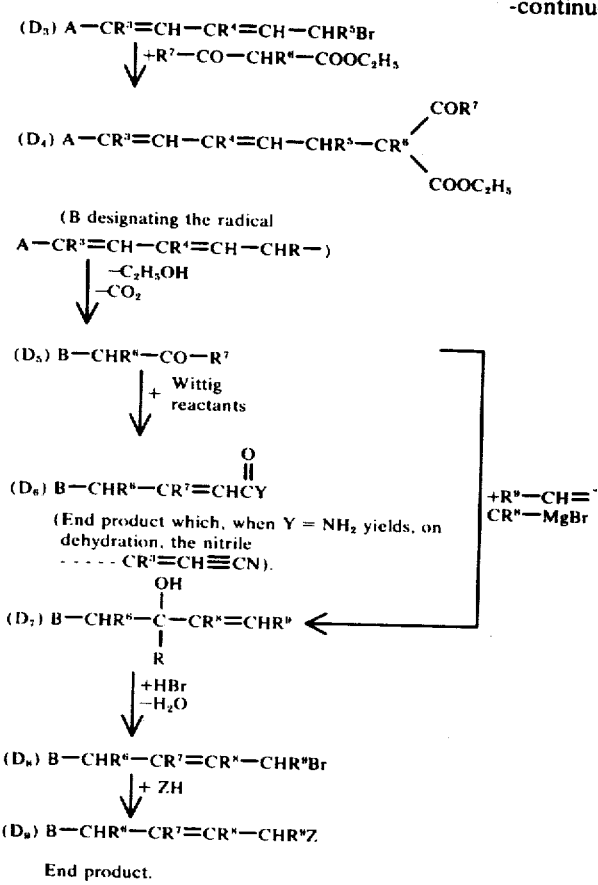

End product.

With regard to scheme A, the only known compounds that are obtainable by reaction of carbon tetrachloride with diolefins are those in which $R_1$=H or $CH_3$.

By reaction with ethyl acetoacetates suitably substituted and by successive decarboxylation ketone $A_3$ unsaturated in the 4 position is obtained from which, by removal of HCl, ketone $A_4$ unsaturated in the 4, 6 positions is obtained by; or, by hydrogenation, re-oxidation of the alcohol formed to saturated ketone, and subsequent removal of HCl, one obtains the unsaturated ketone ω.

It is also possible to react (see scheme B), the carbon tetrachloride with a substituted olefin as described in Italian patent application No. 19,332 A/74. The compound chlorinated in position 1 ($B_1$) formed by removal of HCl, gives the mixture of unsaturated olefins ($B_2$) which, by reaction with the substituted ethyl acetoacetate, gives the unsaturated ketone ω ($B_3$); or the mixture may be saturated with chlorine with the formation of the 2,3-chloro derivative. The latter product, by elimination of HCl, gives mixture ($B_5$) which, by treatment with substituted ethyl acetoacetate and by decarboxylation, gives the unsaturated ketone ω ($B_7$).

From the unsaturated ketones ωA, one proceed reacting those ketones with the suitable magnesium alkenyl bromides (or with alkenyl lithium), as indicated in scheme C; or one may obtain the unsaturated ketone ($D_1$) of scheme D through a Wittig reaction. This latter ketone, through a Grignard reaction using alkenylmagnesium bromide, will give the alcohol as in scheme C ($C_1$) and from which, by reactions analogous to those shown, the compounds of formula (I) can be obtained.

The compounds of this invention are effective against a wide variety of insects, hindering the development of the larval phase to the adult state.

The quantities to be used vary according to the species of insects and to the method of administering the compounds. The active substance may be spread over the natural habitat of the adult insect or spread on its nourishment, or also over the pupae or larvae, or over their habitat, or introduced into their food. In general, the quantities of compounds of this invention which have the desired physiological action, vary from 0.1 parts per million (when administered to the habitat or the food), or from 0.2 γ per insect upward.

Although all the compounds we have prepared have displayed an activity against many species of insects, not all of them have proved to possess the same activity against the same species. There are, that is, some which are particularly active in inhibiting the metamorphosis of one species and less active against another.

Particularly interesting seemed to us the following compounds (all liquids):

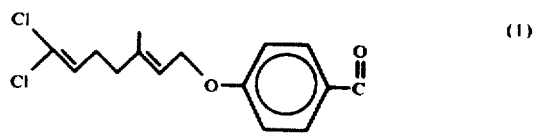

(1)

p-(7,7-dichloro-3-methyl-hepta-2,6-dienyloxy)-acetophenone (our mark 5527); m.w. = 313.19; Cl% = 22.65; liquid soluble in acetone and insoluble in water.

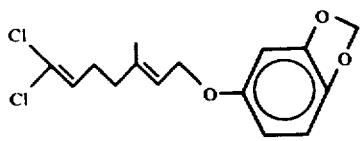

1-(7,7-dichloro-3-methyl-hepta-2,6-dienyloxy)-3,4-methylendioxy-benzene (our mark 5521); m.w. = 315.19; Cl% = 22.50; liquid soluble in acetone and insoluble in water.

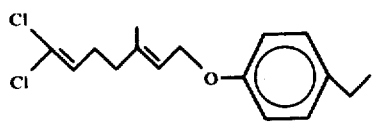

4-(7,7-dichloro-3-methyl-hepta-2,6-dienyloxy)-ethyl-benzene (our mark 5522) — m.w. = 299.33; Cl% = 25.70, soluble in acetone, insoluble in water.

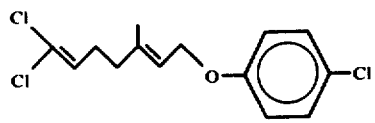

4-(7,7-dichloro-3-methyl-hepta-2,6-dienyloxy)-chloro-benzene (our mark 5523) — m.w. = 305.63; Cl% = 34.80, soluble in acetone, insoluble in water.

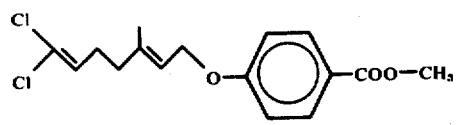

4-(7,7-dichloro-3-, ethyl-hepta-2,6-dienyloxy)-methyl-benzoate (our mark 5524) — m.w. = 329.21 — Cl% = 21.54; insoluble in water, soluble in acetone.

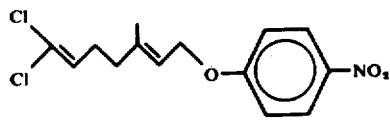

4-(7,7-dichloro-3-methyl-hepta-2,6-dienyloxy)-nitro-benzene (our mark 5526) — m.w. = 316.19; Cl% = 22.43; insoluble in water but soluble in acetone.

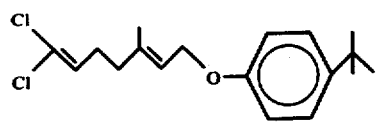

4-(7,7-dichloro-3-methyl-hepta-2,6-dienyloxy)-tert. butylbenzene (our mark 5525) — m.w. = 327.28; Cl% = 21.67; insoluble in water, soluble in acetone.

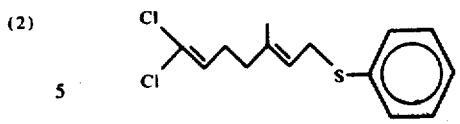

(7,7-dichloro-3-methyl-hepta-2,6-dienylthio)benzene (our mark 5528) — m.w. = 287.25; Cl% = 24.68; insoluble in water but soluble in acetone.

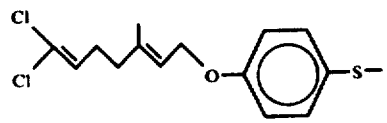

4-methylthio-(7,7-dichloro-3-methyl-hepta-2,6-dienyloxy)-benzene (our mark 5742) — m.w. = 317.27; Cl% = 22.35; insoluble in water but soluble in acetone.

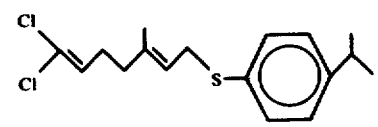

4-(7,7-dichloro-3-methyl-hepta-2,6-dienylthio)-ter.bu-tylbenzene (our mark 5530) — m.w. = 343.35; Cl% = 20.66; insoluble in water, soluble in acetone.

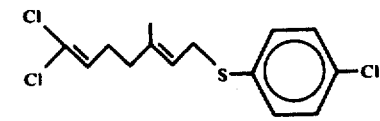

4-(7,7-dichloro-3-methyl-hepta-2,2-dienylthio)-chlorobenzene (our mark 5531) — m.w. = 321.70; Cl% = 33.06; insoluble in water, soluble in acetone.

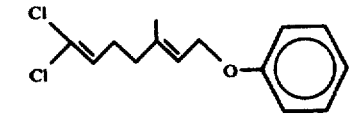

4-(7,7-dichloro-3-methyl-hepta-2,6-dienyloxy)-methylbenzene (our mark 5621) m.w. = 285.20; Cl% 24.86; insoluble in water, soluble in acetone.

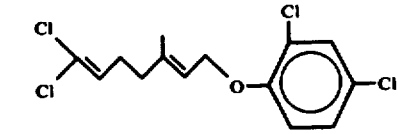

2,4-dichloro-1-(7,7-dichloro-3-methyl-2,6-heptadienyloxy)-benzene (our mark 5713) — m.w. = 340.08; Cl% = 41.70; soluble in acetone but insoluble in water.

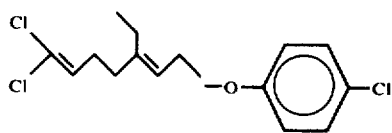

4-(7,7-dichloro-3-ethyl-hepta-2,6-dienyloxy)-chlorobenzene (our mark 6533) — m.w. = 319.66; Cl% = 32.27; insoluble in water, soluble in acetone.

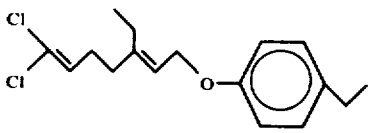

4-(7,7-dichloro-3-ethyl-hepta-2,6-dienyloxy-ethylbenzene (our mark 5631) — m.w. = 313.26; Cl% = 22.64; insoluble in water, soluble in acetone.

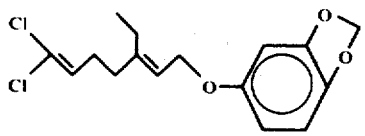

4-(7,7-dichloro-3-ethyl-hepta-2,6-dienyloxy)-3,4-methylendioxybenzene (our mark 5632) — m.w. = 329.21; Cl% = 21.54; insoluble in water, soluble in acetone.

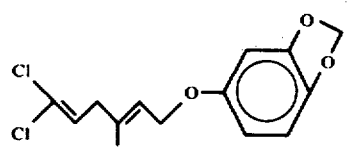

1-(6,6-dichloro-3-methyl-hexa-2,5-dienyloxy)-3,4-methylendioxybenzene (our mark 5714) — m.w. = 301.16; Cl% = 23.54; insoluble in water, soluble in acetone; b.p. 160°/167° C at 0.03 mm Hg.

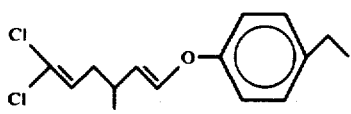

4-(6,6-dichloro-3-methyl-hexa-2,5-dienyloxy)-ethylbenzene (our mark 5717) — m.w. = 285.20; Cl% = 24.86; insoluble in water, soluble in acetone; b.p. = 161°/167° C at 0.03 mm Hg.

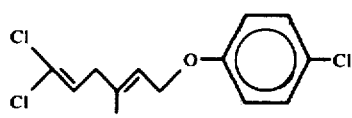

4-(6,6-dichloro-3-methylhexa-2,5-dienyloxy)-chlorobenzene (our mark 5716) — m.w. = 231.60; Cl% = 36.48; insoluble in water, soluble in acetone, b.p. = 158°/163° C at 0.03 mm Hg.

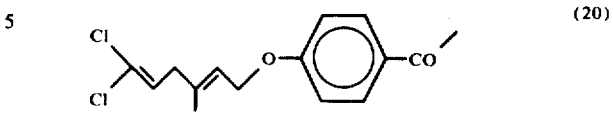

4-(6,6-dichloro-3-methyl-2,5-hexandienyloxy)actetophenone (our mark 5715) — m.w. = 299.19; Cl% = 23.70; insoluble in water, soluble in acetone; b.p. = 165°/172° C at 0.03 mm Hg.

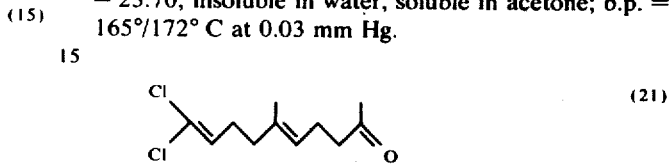

10,10-dichloro-6-methyl-deca-5,9-diene-2 one (our mark 5740) —m.w. = 235.15; Cl% = 30.15; insoluble in water, soluble in acetone; b.p. = 85°/86° C at 0.02 mm Hg.

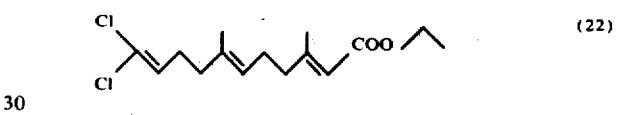

11,11-dichloro-3,7-dimethyl-undeca-2,6,10-ethyl trieneoate (our mark 5738) — m.w. = 305.24; Cl% = 23.23; insoluble in water, soluble in acetone; b.p. = 124°/125° C at 0.02 mm Hg.

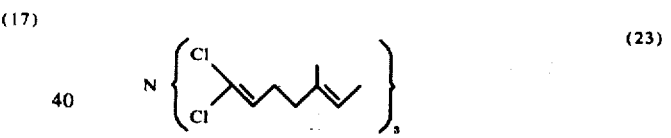

Tris(7,7-dichloro-3-methyl-2,6-heptadienyl)-amine (our mark 5712) — m.w. = 548.25; Cl% = 38.60; N% = 2.55; insoluble in water, soluble in acetone; b.p. = 168°/170° C at 0.02 mm Hg.

11,11-dichloro-3,7-dimethyl-undeca-2,6,10-ethyl trienoate (our mark 5738) — m.w. = 305.24; Cl% = 23.24; b.p. at 0.02 mm Hg = 124°/125° C, liquid insoluble in water, soluble in acetone.

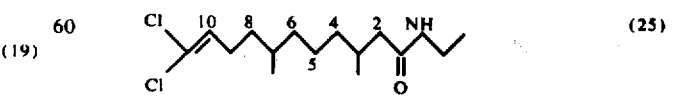

11,11-dichloro-3,7-dimethyl-undeca-2,6,10-triene ethylamide (our mark 5739) — m.w. 304.25; Cl% = 23.31; yellow liquid insoluble in water, soluble in acetone.

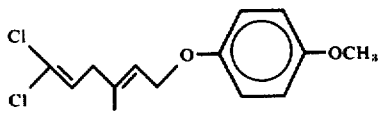
(25a)

P-(6,6-dichloro-3-methyl-hexa-2,5-dienyloxy)-methoxybenzene (our mark 6135) — m.w. = 287.18; Cl% = 24.69; b.p. = 159° to 163° C at 0.03 mm Hg, insoluble in water, soluble in acetone.

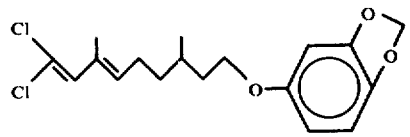
(26)

1-(9,9-dichloro-3,7-dimethyl-nona-2,6,8-trienyloxy)-3,4-methylendioxybenzene (our mark 6288) — m.w. = 355.25; Cl% = 19.96; insoluble in water, soluble in acetone.

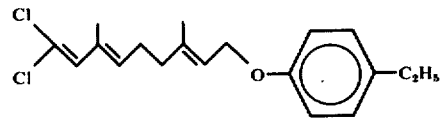
(27)

4-(9,9-dichloro-3,7-dimethyl-nona-2,6,8-trienyloxy)-ethylbenzene (our mark 6351) — m.w. = 339.29; Cl% = 20.9; insoluble in water, soluble in acetone.

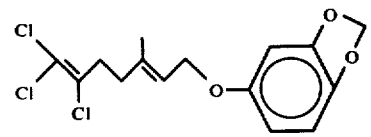
(28)

1,(6,7,7-trichloro-3-methyl-hepta-2,6-dienyloxy)-3,4-methylendioxybenzene (our mark 5905) — m.w. = 349.64; Cl% = 30.42; insoluble in water, soluble in acetone.

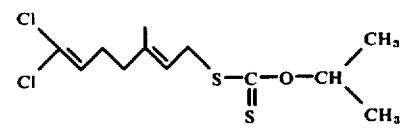
(29)

O-isopropyl-S-(7,7-dichloro-3-methyl-hepta-2,6-dienyl) xantate (our mark 6052) — m.w. = 313.30; Cl% = 22.48; liquid, insoluble in water, soluble in acetone.

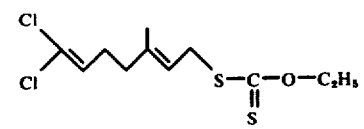
(30)

O-ethyl-S-(7,7-dichloro-3-methyl-hepta-2,6-dienyl) xantate (our mark 6063) — m.w. = 299.28; Cl% = 23.7; liquid, insoluble in water, soluble in acetone.

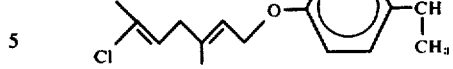
(31)

p.(6,6-dichloro-3-methyl-hexa-2,5-dienyloxy)-isopropylbenzene (our mark 6133) m.w. =299.23; Cl% = 23.7-liquid insoluble in water, soluble in acetone, with b.p. = 166°/169° C at 0.03 mm Hg.

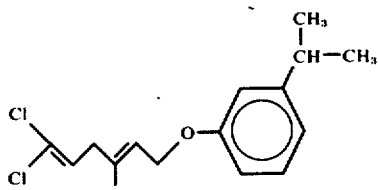
(32)

m-(6,6-dichloro-3-methyl-hexa-2,5-dienyloxy)-isopropylbenzene (our mark 6134) — m.w. = 299.23; Cl% = 23.70; —liquid, soluble in acetone, insoluble in water; b.p. = 167°/170° C at 0.03 mm Hg.

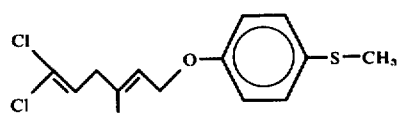
(33)

p-(6,6-dichloro-3-methyl-hexa-2,5-dienyloxy)-thiomethylbenzene (our mark 6140), m.w. = 303.24; Cl% = 23.38; liquid soluble in acetone, insoluble in water, with b.p. = 161°/168° C at 0.02 mm Hg.

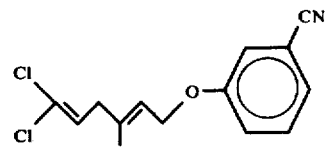
(34)

m-(6,6-dichloro-3-methyl-hexa-2,5-dienyloxy)-benzonitrile (our mark 6136) — m.w. = 282.16; Cl% = 25.13; liquid soluble in acetone, insoluble in water, b.p. = 165°/170° C at 0.03 mm Hg.

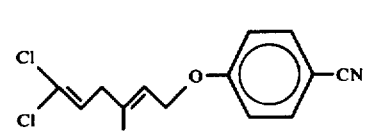
(35)

p-(6,6-dichloro-3-methyl-hexa-2,5-dienyloxy)-benzonitrile (our mark 6137) — m.w. = 202.16; Cl% = 25.13; a liquid soluble in acetone, insoluble in water.

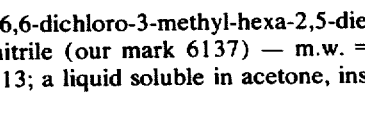
(36)

1,1-dichloro-5-methyl-8,11-dioxatrideca-1,5-diene (our mark 5979) — m.w. = 267.19; Cl% = 26.54; a liquid soluble in acetone but insoluble in water.

(37)

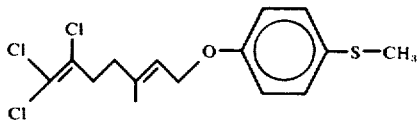

p-(6,7,7-trichloro-3-methyl-hepta-2,8-dienyloxy)-thiomethylbenzene (our mark 5912) — m.w. = 351.73; Cl% = 30.24; a liquid soluble in acetone, but insoluble in water, b.p. = 175°/180° C at 0.02 mm Hg.

(38)

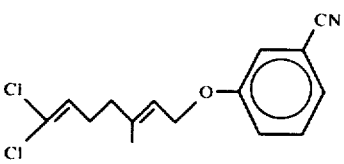

m-(7,7-dichloro-3-methyl-hepta-2,6-dienyloxy)-benzonitrile (our mark 6066) — m.w. = 296.19; Cl% = 23.94; a liquid insoluble in water but soluble in acetone.

(39)

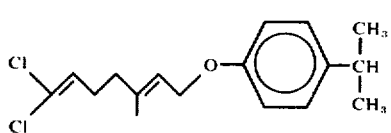

p-(7,7-dichloro-3-methyl-hepta-2,6-dienyloxy)-isopropylbenzene (our mark 5953) — m.w. = 313.26; Cl% = 22.64; a liquid insoluble in water but soluble in acetone; b.p. = 136°/143° C at 0.04 mm Hg.

(40)

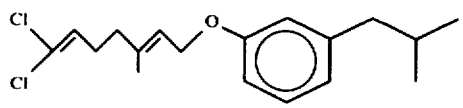

4-(7,7-dichloro-3-methyl-hepta-2,6-dienyloxy)-sec.butylbenzene (our mark 5977) — m.w. = 327.28; Cl% = 21.67; a liquid insoluble in water but soluble in acetone; b.p. = 145°/147° C at 0.04 mm Hg.

(41)

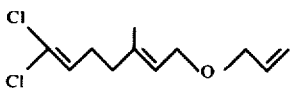

1,1-dichloro-5-methyl-8-oxa-endeca-1,5,10-triene (our mark 5983) molecular weight = 235.15; Cl% = 30.15; light yellow liquid soluble in acetone, insoluble in water.

The new compounds of this invention, and the intermediates for the production thereof, have been identified by elementary analysis and by examination of the MNR, IR and UV spectra. They were purified by liquid gas chromatography or as a thin layer on silica gel, and are mixtures of cis- and trans- isomers in various ratios.

The hormonal activity of the compounds according to this invention has been tested on the following species of insect:

Tenebrio molitor, Pieris brassicae, Spodotera littoralis, Angasta Kubniella, Tribolium consum, Aedes aegypti, Musca domestica, as described in Example 57.

The following examples, which show the preparation of the new compounds of the invention and the biological activity thereof, are given to illustrate the invention and are not intended to be limiting.

EXAMPLE 1

Mixture of 1,1,1-trichloro-prop-2-ene, and 1,3,3-trichloro-prop-2-ene.

In a 2 liter flask, 364 g of 1,1,1-tetrachloropropane (prepared from ethylene and $CCl_4$, as described in Journal Chemical Society 1963, 1887, by M. Asscher & D. Vofsi) and 100 ml of ethyl-cellosolve where slowly additioned, under stirring, with 134 g of an 85% KOH ml of ethyl-cellosolve, the reaction temperature being maintained between −5° C and 0° C for 6 hours and at 15° C for 30 minutes. Thereupon, the reaction mixture was poured into water and ice and was left to decant overnight.

The organic layer was separated and added to the etheric extracts of the aqueous phase and the whole was dried on $Na_2SO_4$ and the ether was evaporated at reduced pressure. The residue was then distilled to obtain 191 g of a mixture containing 77% of $CCl_3CH:CH_2$ and 23% of $CCl_2:CHCH_2Cl$ (see A.N. Nesmeyanov et al. Izvest. Akad. Nauk. S.S.S.R. Otdel. Khim. Nauk 1951, 505–511; CA46, 7034b), and 63 g of a mixture containing 5% of $CCl_3CH:CH_2$ and 95% of $CCl_2:CHCH_2Cl$; both fractions were usable for subsequent synthesis operations.

EXAMPLE 2

2-acetyl-5,5-dichloro-pent-4-ethylenoate

Into a flask of 1 lt holding capacity were introduced 200 ml of anhydrous tetrahydrofuran and 28.1 g of a 55% (b.w.) mixture of sodium iodide in mineral oil.

Under stirring and being careful not to exceed 33° C, into the flask were introduced 33.6 g of ethyl acetoacetate and then 93.4 g of a mixture of $CCl_3CH:CH_2$ (77%) and $CCl_2:CH_2Cl$ (23%).

The reaction mixture was then refluxed for 8 hours and left standing at room temperature for 12 hours. The greatest part of the tetrahydrofuran was then evaporated at reduced pressure and the residue was poured into water. After decanting, the organic base was separated and the aqueous phase was extracted with two portions of 100 ml of $CH_2Cl_2$. The organic phases put together were then washed with water and dried on $Na_2SO_4$. After evaporation at reduced pressure of the $CH_2Cl_2$, the distillation of the residue yielded 90 g of 2-acetyl-5,5-dichloro-pent-4-ethyl enoate (b.p. = 85°–87° C at 0.1 mm Hg.

EXAMPLE 3

6,6-dichloro-es-5-en-2-one 78.4 g of the keto-ester prepared above where dripped into a solution of 21.6 g of KOH (85%) in 400 ml of $H_2O$, after which the mixture was stirred at room temperature until the ester was completely dissolved (abt. 4hours).

The possibly unreacted ester was then extracted with two portions of 100 of ethyl ether each, and the aqueous solution was acidified with 50 % $H_2SO_4$. This solution was refluxed for 1 hour. After cooling down, extraction was carried out with ethyl ether (3 portions of 100 ml each); it was then washed with water, with sodium bicarbonate, and again with water, and finally it was dried on Na₂SO₄. The evaporation of the ether left an oily residue which was distilled under vacuum. Thereby, 45.4 g of 6,6-dichloro-es-5-en-2-one (b.p. = 50° C at 0.04 mm Hg) were obtained.

EXAMPLE 4

7,7-dichloro-3-methyl-1,6-heptadien-3-ol

Into a 1 lt flask were introduced 7.6 g of Mg turnings which were covered with 80 of anhydrous tetrafuran. Then under stirring and under a nitrogen atmosphere, dropwise, there were additional 35 g of vinyl bromide in 70 of anhydrous tetrahydrofuran, in such a way that the temperature would not exceed 40°–50° C. After the addition had been completed, the mixture was heated under refluxing for 30 minutes and then cooled down to room temperature and a solution of 45.4 g of 6,6-dichloro-es-5-en-2-one in 50 ml of anhydrous tetrahydrofuran was dripped into the cooled solution, being careful not to exceed 30° C.

After 12 hours at room temperature, the mixture was hydrolized with ice and ammonium chloride. The reaction mixture was then decanted, extracted with ethyl ether, washed with water and finally dried on Na₂SO₄. After evaporation of the solvent, and after distillation, 43 g of 7,7-dichloro-3-methyl-1, 6-heptadien-3-holo (b.p. = 68°–72° c at 0.035 mm Hg) were obtained.

EXAMPLE 5

1,1-dichloro-7-bromo-5-methyl-1,5-heptadien trans-cis mixture 28.9 g of the previously obtained tertiary alcohol were added, at 0°–5° C, to a solution of 24.8 g of HBr in 110 ml of CH₃COOH. After stirring for 30 minutes at 0° C, the reaction mixture was poured into water and ice and the organic layer was separated and additioned with the etheric extract of the aqueous phase. It was then washed with an aqueous solution of 10% Na₂CO₃. and then with water until attaining neutralization. After drying on Na₂SO₄, evaporation of the ether at reduced pressure and distillation under vacuum, there were obtained 33 g of 1,1-dichloro-7-bromo-5-methyl-1,5-heptadiene (b.p. =85°–92° C at 0.05 mm Hg.). The gas-liquid chromatography analysis showed the presence of 2 stereoisomers: trans isomer 62%, cis isomer 38%.

EXAMPLE 6 p-(7,7-dichloro-3-methyl-2,6-heptadienyloxy)-acetophenone 2.04 g of p-hyroxyacetophenone in 10 ml of EtOH were added to a solution of 1 g of KOH (85%) in 20 ml of EtOH. To the mixture thus obtained, were then added 3.87 g of 1,1-dichloro-7-bromo-5-methyl-1,5-heptadiene as prepared above. This reaction mixture was then stirred for 3 hours at the reflux temperature of ethanol.

After cooling down the precipitated KBr was filtered and the greatest part of the alcohol was evaporated at reduced pressure. The residue was then poured into water and the water was extracted with 3 portions of 50 ml of ethyl ether each. The etheric solution was washed with NaOH and then with water until reaching neutrality.

After drying on Na₂SO₄ and decoloring with active coal, the ether was evaporated at reduced pressure until reaching a constant weight of the residue. Thereby 4 g of a mixture were obtained which consisted of 40% of cis and of 60% of trans -p-(7,7-dichloro-3-methyl-2,6-heptadienyloxy)- acetophenone.

EXAMPLES 7–23

Operating as in the preceding example (6), by condensing the suitable phenols with 1,1-dichloro-7-bromo-5-methyl-1,5-heptadiene, prepared as described in Example (5), the following aromatic ethers (or thioethers) were obtained:

7. 1-(7,7-dichloro-3-methyl-hepta-2,6-dienyloxy)-3,4-methylendioxy-benzene from 3,4-methylendioxyphenol.
8. 4-(7,7-dichloro-3-methyl-2,6-heptadienyloxy)-ethylbenzene from p-ethylphenol.
9. 4-(7,7-dichloro-3-methyl-2,6-heptadienyloxy)-chlorobenzene from p-chlorophenol.
10. 4-(7,7-dichloro-3-methyl-2,6-heptadienyloxy)-methylbenzoate from methyl p-hydroxybenzoate.
11. 4-(7,7-dichloro-3-methyl-2,6-heptadienyloxy)-nitrobenzene from p-nitrophenol.
12. 4-(7,7-dichloro-3-methyl-2,6-heptadienyloxy)-terbutylbenzene from p-ter-butylphenol.
13. (7,7-dichloro-3-methyl-2,6-heptadienyloxy)-benzene from thiophenol.
14. 4-methylthio-(7,7-dichloro-3-methyl-2,6-heptadienyloxy)-benzene from 4-methylthiophenol.
15. 4-(7,7-dichloro-3-methyl-2,6-heptadienyloxy)-terbutylbenzene from p-ter-butylthiophenol.
16. 4-(7,7-dichloro-3-methyl-2,6-heptadienyloxy)-chlorobenzene from p-chlorothiophenol.
17. 4-(7,7-dichloro-3-methyl-2,6-heptadienyloxy)-methylbenzene from p-methylphenol.
18. 1-(7,7-dichloro-3-methyl-2,6-heptadienyloxy)-3-methoxybenzene from m-methoxyphenol.
19. 3-(7,7-dichloro-3-methyl-2,6-heptadienyloxy)-methylbenzene from 3-methylphenol.
20. 3-(7,7-dichloro-3-methyl-2,6-heptadienyloxy)-nitrobenzene from 3-nitrophenol.
21. 2,4,6-trichloro-1-(7,7-dichloro-3-methyl-2,6-heptadienyloxy) benzene from 2,4,6-trichlorophenol.
22. 1-(7,7-dichloro-3-methyl-2,6-heptadienyloxy)-4-phenylbenzene from 4-phenylphenol.
23. 2,4-dichloro-1-(7,7-dichloro-3-methyl-2,6-heptadienyloxy)-benzene from 2,4-dichlorophenol.

EXAMPLE 24

2-propionyl-5,5-dichloro-pent-4-ethyl enoate

Operating as described in example (2), from 50 g of ethyl-3-oxo-pentanote (prepared according to Anderson et al - Journal American Chemical Society 67, 2197, 1954) and 50.9 g of a mixture containing 60% of CCl₃CH:CH₂ and 40% of CCl₂:CH-CH₂Cl there were obtained 46 g of 2-propionyl-5,5-dichloro-pent-4-ethyl enoate with a b.p. = 94°–97° C at 0.07 mm Hg.).

EXAMPLE 25

7,7-dichloro-hept-6-en-3-one

Operating as described in Example (3), from 39 g of the keto ester prepared above there were obtained 23 g of 7,7-dichloro-hept-6-en-3-one with a b.p. =57°–61° c at 0.07 mm Hg.

EXAMPLE 26

7,7-dichloro-3-ethyl-1,6-hept-dien-3-ol

Operating as described in Example 4, from 17.7 g of 7,7-dichloro-hept-6-en-3-one there were obtained 15.3 g of 7,7-dichloro-3-ethyl-1,6-heptadiene-3-ol (b.p. = 64°–69° c at 0.03 mm Hg.).

EXAMPLE 27

1,1-dichloro-7-bromo-5-ethyl-1,5-heptadiene (A)

Operating as described in Example (5), from 12 g of the tertiary alcohol prepared as above there were obtained 15 g of 1,1-dichloro-7-dichloro-7-bromo-5-ethyl-1,5-heptadiene (trans 62%, cis38%) (A).

EXAMPLES 28-30

7,7-dichloro-3-ethyl-2,6-heptadien-1-yl arylesters 28. 4-(7,7-dichloro-3-ethyl-2,6-heptadienyloxy)-chlorobenzene from (A) and p-chlorophenol.
29. 4-(7,7-dichloro-3-ethyl-2,6-heptadienyloxy-ethyl-benzene from (A) and p-ethylphenol.
30. 1-7,7-dichloro-3-ethyl-2,6-heptadienyloxy)-3,4-methylendioxy-benzene from (A) and 3,4-methylen-dioxyphenol.

The products were obtained operating as in Example 6.

EXAMPLE 31

6,6-dichloro-3-methyl-1,5-hexadienyl-3-ol

Operating according to Example (4), from 39 g of 5,5-dichloropent-4-en-2-one (prepared as described in Ann. Chem., 1972, 7, 411 by F. De Champs De St. Leger), from 30 g of vinyl bromide and 150 ml of tetrahydrofuran there were obtained 40 g of 6,6-dichloro-3-methyl-2,5-hexadienyl-3-ol with a b.p. = 87°–73° C at 17 mm Hg.

EXAMPLE 32

1,1-dichloro-6-bromo-4-methyl-1,4-hexadiene

Operating as described in Example (5), from 12 g of 6,6-dichloro-3-methyl-2,5-hexadienyl-3-ol and 9.6 g of HBr in 50 ml of acetic acid, there were obtained 17 g of a mixture of stereo-isomers (79% trans, 21% cis- of 1,1-dichloro-6-bromo-4-methyl-1,4-hexadiene.

EXAMPLES 33 - 38

Preparation of 6,6-dichloro-3-methyl-2,5-hexadienyl aryl esters

Operating as described in Example (6), by condensing the suitable phenols with 1,1-dichloro-6-bromo-4-methyl-1,4-hexadiene, the following aromatic ethers were obtained:

33. 1-(6,6-dichloro-3-methyl-2,5-hexadienyloxy)-3,4-methylene-dioxybenzene from 3,4-methylendioxyphenol.
34. 4-(6,6-dichloro-3-methyl-2,5-hexadienyloxy)-ethylbenzene from p-ethylphenol.
35. 4-(6,6-dichloro-3-methyl-2,5-hexadienyloxy)-chlorobenzene from p-chlorophenol.
36. 4(6,6-dichloro-3-methyl-2,5-hexadienyloxy)-methylbenzoate from p-hydroxy-methylbenzoate.
37. 1-(6,6-dichloro-3-methyl-2,5-hexadienyloxy)-2,4-dichlorobenzene from 2,4-dichlorophenol.
38. 4-(6,6-dichloro-3-methyl-2,5-hexadienyloxy)-acetophenone from p-hydroxyacetophenone.

EXAMPLE 39

2-acetyl-9,9-dichloro-5-methyl-4,8-ethyl nonadienate 13 g of ethyl acetoacetate were dripped into a suspension of 4.4 g of NaH (55% in mineral oil) in 50 ml of anhydrous tetrahydrofuran (THF). To the resulting solution were then added 25.8 g of 1,1-dichloro-7-bromo-5-methyl-1,5-heptadiene dissolved in 50 ml of anhydrous THF.

This reaction mixture wad reflux-heated for 5 hours and then cooled down to room temperature.

The greatest part of the THF was removed under reduced pressure and the residue was taken up in water. The raw ester separated from the aqueous phase and the etheric extract of the aqueous phase were mixed together and dried on $NaSO_4$. The solution was then filtered and the ether removed under reduced pressure. The residue was distilled to obtain 27 g of keto-ester with a b.p. = 125°–128° C at 0.02 mm Hg.

EXAMPLE 40

10,10-dichloro-6-methyl-5,9-decadien-2-one

Following the procedure described in Example 3, from 25 g of keto ester as prepared above were obtained 15 g of a ketone having a b.p. = 85°–88° C at 0.02 mm Hg.

EXAMPLE 41

11,11-dichloro-3,7-dimethyl-2,6,10-ethyl-undecatrienoate 4.6 g of methyl diethoxy-acetophosphonate in 30 ml of THF were added to a suspension of NaH (0.49) in 50 ml of THF. This suspension was then stirred for 1 hour after which there were added 4.4 g of 10, 10-dichloro-6-methyl-5,9-decadien-2-one in 20 ml of THF. The stirring was carried on for 1 hour at 45° C and for 12 hours at (on $Na_2SO_4$) and after evaporation of the ether used in the extraction, there was obtained a residue which distilled gave 3.8 g of 11, 11-dichloro-3,7-dimethyl-2,6,10-ethyl-undecatrienoate with b.p. =124°–125° C at 0.03 mm Hg.

EXAMPLE 42

1,1-dichloro-1,3-octadien-7-one 65 g of 1,1,1,-trichloro-3-octen-7-one (prepared as described by W.J. Pyne in Journal Org. Chem. 27, 3483, 1962) were mixed with 110 ml of dicyclohexylamine and the resulting mixture was reflux-heated for 3 hours and then left standing for 12 hours at room temperature.

After filtering of the $(C_6H_{11})_2N^+H_2Cl^-$ precipitate, the reaction mixture was diluted with ethyl ether and then repeatedly washed with acidulated water. The etheric solution dried on $MgSO_4$ was concentrated at reduced pressure and then distilled, giving 52.0 g of 1,1-dichloro-1,3-octadien-7-one with a b.p. = 70°–73° C at 0.02 mm Hg.

EXAMPLE 43

Tris-(7,7-dichloro-3-methyl-2,6-heptadienyl)-amine

Into a rocking stainless steel autoclave of 100 ml holding capacity were loaded, at −30° C, 30 g of 7-bromo-1,1-dichloro-5-methyl-1,5-heptadiene, 2.5 ml benzene and 18 g of $NH_3$. The autoclave was then brought up to room temperature in 2 hours and heated at 80° C for 4 hours. After cooling down, the autoclave was opened and the content was washed with aqueous NaOH. The organic layer was separated, dried (on $Na_2SO_4$) and, after evaporation of the benzene at reduced pressure, was distilled to yield 20 g of the tertiary amine (b.p = 168–170 C at 0.02 mm Hg.).

EXAMPLE 44

Biological activity

The tests were carried out in a conditioned environment on the following species of insects:

*Tenebrio molitor, Pieris brassicae, Spodoptera littoralis, Anagasta kuemniella, Tribolium confusum. Aedes aegypti, Musca domestica.*

The conditions under which the tests were conducted are indicated in the following for each species in the given order.

1. *Tenebrio m.* — Pupae aged from 0–24 hours were treated by topical application on the antepenultimate urosternite with an acetone solution of the product (2 cu.mm).

The results were appraised after 9 days, when the insects of the test group had completely emerged from the cocoons.

2. *Pieris bass.* — Larvae of the last age were treated by topical application on the first urosternites with an acetone solution of the product (2 cu.mm).

Appraisal of the results was carried out every 5 days approximately up to the complete emergence from the cocoons of the adult insects.

3. *Spodoptera l.* — Larvae of the last age were treated by topical application on the first urosternites with an acetone solution of the product (2 cu.mm). The results were appraised about every 5 days until complete emergence from the cocoons of adult insects.

4. *Anagasta k.* — 5 g of maize meal were uniformly treated with an acetone solution of the product. Twenty-four hours after the treatment the meal was infested with 21 days larvae.

Appraisal of the results was made every 3–4 days, starting from the beginning of the appearance of the adults up to the end of the emergence thereof from the cocoons.

5. *Tribolium c.* —5 grams of wheat meal were uniformly treated with an acetone solution of the product. After 24 hours, the meal was infested with 22 days larvae. Appraisal of the results was made after about 45 days, when the insects of the test group had completed their emergence from the cocoons.

6. *Musca d.* —5 grams of sugar and 5 g of a mixture of sugar, milk and powdered egg yolk, were treated separately with an acetone solution of the product. After evaporation of the solvent, the sugar and the mixture introduced separately into two beakers together with adult flies —25 males and 25 females. Subsequently, the above indicated egg-based mixtures was administered to flies fed with the treated sugar but not treated with the products under examination. After the first egglaying, 100 eggs were transferred to pabulum. After 2 days the percentage of hatched eggs was ascertained; after a further 5 days the pupae were gathered and counted; and after another 4 days the percentage of adults which had emerged from the cocoons was determined.

7. *Aedes aegypti* —3 cc of an acetone solution of the product were added to 297 cc of spring water into which were subsequently transferred 254-days larvae supplying them with the proper nourishment. Appraisal of the results was made every 2-3 days up to end of the emergence from the cocoons in the test group.

Criteria for evaluating the activity for the insects tests: 1,2,3,4,5 and 7

The activity index adopted was the ratio, in percent, of dead individuals and ill shaped and abnormal individuals with respect to the number of treated individuals, according to the following formula:

$$activity = \frac{individuals(dead + illshaped + abnormal)}{treated\ individuals}\%$$

Criteria for evaluating the results of the test with Musca domestica (6)

The activity index adopted was percentual ratio of unhatched eggs with respect to the total of the eggs laid by the insects treated, as indicated by the following formula:

$$activity = \frac{unhatched\ eggs}{total\ of\ eggs\ laid}\%$$

EXAMPLE 45

Preparation of mixture (E) -1,5,5,5-tetrachloro--2-methyl-pent-2-ene, and (E) - 1,5,5,5-tetrachloro-3-methyl-pent-2-ene (Scheme A above).

Reaction:

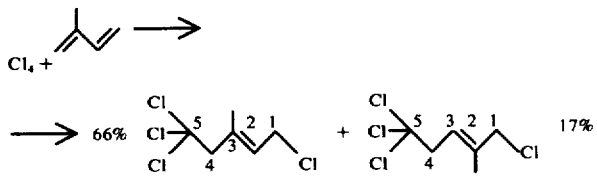

Into a 500 ml stainless autoclave was loaded a mixture of $CCl_4$(153 g; 1 mole), isoprene, (34.1 g; 0.5 mole), $CH_3CN$ (39 g; 0.94 mole), $CuCl_2.2H_2O$ (0.85 g) and n-butylamine (0.875g).

After 6 hours at 130° C, the autoclave was cooled down and the content was recovered. From two identical tests there were obtained 433 g of a dark oil which, after concentration at reduced pressure, washing with water and subsequent drying, gave 213 g of a mixture containing 17% by weight of (E) —1,5,5,5-tetrachloro-2-methyl-pent-2-ene and 66% b.w. of (E) —1,5,5,5,-tetrachloro-3-methyl-pent-2-ene. Said mixture had a b.p. comprised between 116° and 118° C at 20 mm Hg.

The separation of the two isomers was carried out by means of gas chromatography while the identification was determined by anaylsis of the R.M.N. spectrum.

EXAMPLE 46

Preparation of (E) 2-acetyl-7,7,7-trichloro-5-methyl-hept-4-ethyl enoate (Scheme A).

Reaction:

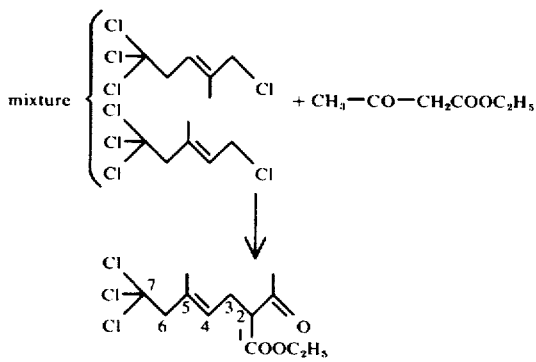

Into a 1 lt, flask were loaded 250 ml of anhydrous tetrahydrofuran and 9.8 g (0.224 mole) of NaH in a 50% b.w. mixture in mineral oil.

Under mild stirring, and being careful not to exceed 33° C, 292 g (0.244 mole) of ethyl acetoacetate, and then 55 g of the isomer mixture of Example 1 (respectively 0.087 mole and 0.161 mole) were introduced into the flask. The mixture was then refluxed for 8 hours, after which it was left standing for 12 hours at room temperature.

Thereupon the tetrahydrofuran was evaporated at reduced pressure and the residue was poured into water. There separated an organic phase which was added to the extracts from the water with $CH_2Cl_2$. After drying of the extracts in organic solvent on $Na_2SO_4$ and evaporation under vacuum, by distillation of the residue under vacuum there was obtained an oil (42 g; 0.133 mole) consisting of (E) -2-acetyl-7,7,7-trichloro-5-methyl-hept4-ethyl enoate with a b.p. = 108°–110° C at 0.001 mm Hg. The product, purified by gas-chromatography, was identified on the basis of the M.N.R. spectrum.

EXAMPLE 47

Preparation of (E) -8,8,8-trichloro-6-methyl-oct-5-cn2-one (Scheme A)

Reaction:

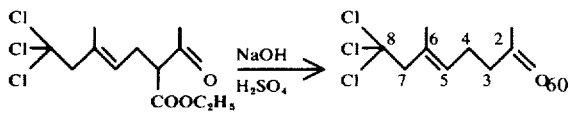

Into a solution of 7.8 g of 85% KOH in 100 ml of $H_2O$ were dripped 37.5 g (0.119 mole) of 2-acetyl-7,7,7-trichloro-5-methyl-hept-4-ethyl) enoate. The mixture was stirred at room temperature until the ester was completely dissolved (about 4 hours), and then extracted with ethyl ether in order to remove the unreacted ester.

The aqueous phase was acidified with 30 g of $H_2SO_4$ at 50%. It was then refluxed for 1 hour and, after cooling down, it was extracted with ether.

The ether extracts, washed with water and dried or anhydrous $Na_2SO_4$ were evaporated under vacuum. The residue, distilled under vacuum gave an oil (11.6 g; 0.0475 mole) having a b.p. between 70° and 72° C at 0.1 Hg, besides 22.6 g of unreacted ketoester.

The oil, purified by gas-chromatography, was identified as (E)--8,8,8-trichloro-6-methyl-oct-5-en-2-one on the basis of the M.N.R. spectrum.

EXAMPLE 48

Preparation of (E) -8,8-dichloro-6-methyl-octa-5,7-dien-2-one (Scheme A)

Reaction:

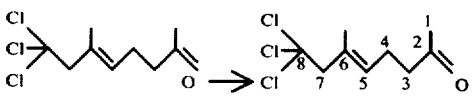

18 g (0.074 mole) of the trichloro-ketone obtained according to the preceding example, were mixed with 30 g (abt. 0.15 mole) of dicyclohexylamine, and the resulting mixture was then heated in a nitrogen atmosphere for 4 hours at 200° C. After the mixture had stood for 12 hours under a nitrogen atmosphere at room temperature, the dicyclohexylamine chlorohydrate that formed was filtered, the liquid was diluted with ethyl ether and was then repeatedly washed with acidulated water.

The ether solution, dired on $MgSO_4$, was evaporated under reduced pressure and then distilled under vacuum. There were obtained 8 g (0.039 mole) of (E) -8,8-dichloro-6-methyl-octa-5,7-dien-2-one having a b.p. at 0.1 mm Hg comprised between 72° and 74° C. The product was purified by gas-chromatography and was identified on the basis of the M.N.R. spectrum.

EXAMPLE 49

Preparation of 9,9-dichloro-3,7-dimethyl-nona-1,6,8-trien-3-ol (Scheme C)

Reaction:

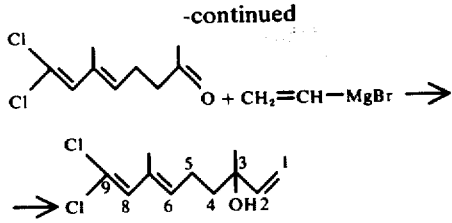

Into a 500 cc flask were introduced 2.9 g of magnesium turnings which were covered with 30 cc of anhydrous tetrahydrofuran. Under stirring and in a nitrogen atmosphere there were added dropwise, 12.8 g of vinyl bromide in 15 ml of anhydrous tetra hydrofuran so that the temperature would not exceed 40°–50° C.

After said addition, the mixture was reflux-heated for 30 minutes, then brought back to room temperature and into it was dripped a solution of 9 g of (E) -8,8-dichloro-6-methyl-octa-5,7-dien-2-one in 20 ml of anhydrous tetrahydrofuran, without exceeding 30° C. On completion of this operation, the mixture was left standing for 24 hours at room temperature, after which the reaction mixture was hydrolized with ice and ammonium chloride.

The mixture was then decanted, extracted with ethyl ether, the extract was washed with water and dried on anhydrous $Na_2SO_4$.

After evaporation of the solvent and subsequent distillation, there were obtained 9.8 g of a product boiling at 80°–85° C at 0.001 mm Hg and which was identified as 9,9-dichloro-3,7-dimethyl-nona-1,6,8-trien-3-ol on the basis of its M.N.R. spectrum.

EXAMPLE 50

Preparation of 1-bromo-9,9-dichloro-3,7-dimethyl-nona-2,6,8-triene (Scheme C)

Reaction:

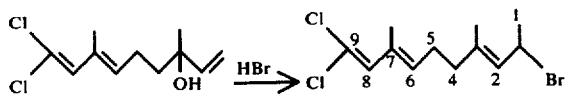

8.8 g of the alcohol of the preceding example were added to a solution of 16 g of HBr in 53 g of glacial acetic acid, at 0° C–5° C.

After stirring at 0° C for 1 hour, the reaction mixture was poured into water and ice and the organic layer was separated and additioned to the ether extract of the aqueous phase. It was subsequently washed with a 10% b.w. aqueous solution of $Na_2CO_4$ and then with water until attaining neutrality. The product was then dried on $Na_2SO_4$, the ether was evaporated at reduced pressure and finally it was distilled under vacuum. Thereby 15.8 g of oil were obtained which had a b.p. of 80°–100° C at 0.001 mm Hg. At the M.N.R. spectrography the product appeared to consist of 70% b.w. of the isomer 1-bromo-9,9-dichloro-3,7-dimethyl-nona-(E)-2, (E) -6, (E) -8-triene and of 30% b.w. of the isomer 1-bromo-9,9-dichloro-3,7-dimethyl-nona-(Z)-2,(E) -6, (E)-8-triene.

EXAMPLE 51

Preparation of 1-(9,9-dichloro-3,7-dimethyl-nona-2,6,8-trienyloxy)-3,4-methylen dioxybenzene (our mark 6288)

Reaction:

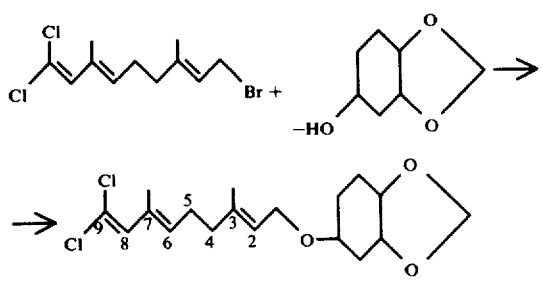

Under stirring and in an inert atmosphere, 4.1 g of 3,4-methylendioxy-phenol were added to a suspension of $K_2CO_3$(4.1 g) in dimethylformamide (20 cc).

The mixture was cooled down to 0° C and additioned with 5.1 g of the bromide of the preceding example. The mixture was stirred for 12 hours at 0° C, after which it was poured into ice. The organic residue that separated and the ether extracts of the aqueous phase, put together, were decolored with active coal and then concentrated at reduced pressure. Thereby 4.4 g of 1-(9,9-dichloro-3,7-dimethyl-nona-2,6,8-trienloxy)-3,4-methylendioxybenzene were obtained; theoretical Cl = 19.96%; found Cl = 21,36%.

The M.N.R. spectrum, compatible with the foreseen structure, was obtained on a product purified by preparatory thin-layer gas-chromatography (carrier: Merck silica gel; solvents; n-hexane-ethyl ether (90:10).

EXAMPLE 52

Preparation of a mixture of 2,3,3,3-tetrachloroprop-1-ene with 1,1,2,3-tetrachloroprop-1-ene (Scheme B)

Reaction:

-continued

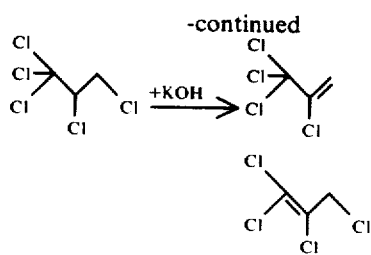

Preparation of 1,1,1,2,3-pentachloropropane according to Hene & Whaley — Journal American Chemical Society 64 (1942) page 1158

276 g (121 mole) of 1, 1, 1, 2, 3-pentachloropropane, with b.p. of 192.5°–193° C at atmospheric pressure and at a concentration of 25% in 100 ml of ethanol, were dehydrohalogenated with 88 g (1.33 mole) of 85% KOH in 350 ml of ethanol at 0° C for 6 hours. The reaction mixture was then poured into water and ice and left to decant overnight. The organic layer that separated, together with the ether extracts of the water, was dried on $Na_2SO_4$ and the solvent was evaporated at reduced pressure.

The distilled residue yielded 153.3 g (0.85 mole, 70%) of a mixture (with a b.p. = 43°–54° C at 19 mm Hg) containing 70% b.w. of 2,3,3,3-tetrachloropropene and 30% b.w. of 1,1,2,3-tetrachloroprop-1-ene.

EXAMPLE 53

Preparation of 2-acetyl-4,5,5-trichloro-pent-4-ethyl enoate (Scheme B)

Reaction:

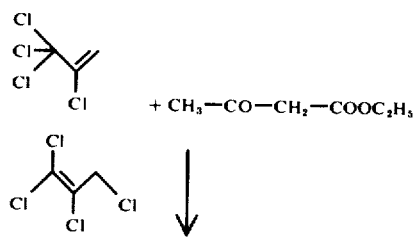

Into a 1 liter flask there were introduced 500 ml of anhydrous tetrahydrofuran and 34 g of N aH (55% in mineral oil). Under stirring and being careful not to exceed 30° C, there were added 101 g of ethyl acetoacetate, and subsequently 145 g of the mixture of chloropropenes obtained as described in the preceding example. The mixture was refluxed for 8 hours and then left to rest for 12 hours at room temperature. After evaporation of the tetrahydrofuran at reduced pressure, the residue was poured into water. After decanting, the organic phase separated and the aqueous phase was extracted with dichlormethane.

The organic phases were combined and washed with water, dried on a solid dehydrating agent and then evaporated at reduced pressure. By distillation of the residue under vacuum 185 g (0.68 mole) of 2-acetyl-4,5,5-trichloro-pent-4-ethyl enoate were obtained having a b.p. = 85°–87° C at 0.1 mm Hg. It was used as such for the subsequent reaction.

EXAMPLE 54

Preparation of the 5,6,6-trichloro-es-5-en-2-one. (Scheme B)

Reaction:

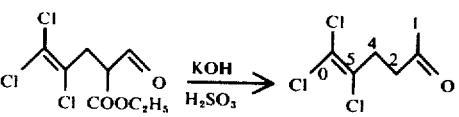

The raw 2-acetyl-4,5,5-trichloro-pent-4 ethyl enoate prepared according to example 9 (185 g; 068 mole), was dripped into an 85% KOH solution (21.6 g) in 400 ml of $H_2O$. The solution was stirred at room temperature until the ether was dissolved (4 hours), the unreacted ether was extracted with two portions of 50 ml each of ethyl ether, and finally the separated aqueous phase was acidified with 50% $H_2SO_4$. It was then reflux-boiled for 1 hour. After cooling down, the ethyl ether was extracted (with 3 portions of 100 ml each), the ether extract was washed with water, with a sodium bicarbonate solution and then again with water, until neutrality was attained and, finally, it was dried on $Na_2SO_4$. The evaporation of the ether left, as residue, an oil (83 g; 0.414 mole) having a b.p. = 67.5° C at 10.15 mm Hg.

A sample of the product, purified by gas-chromatography and subjected to M.N.R. analysis, appeared to consist of 5,6,6-trichloro-es-5-en-2-one.

EXAMPLE 55

Preparation of 6,7,7-trichloro-3-methyl-1,6-hepta-dien-3-ol (Scheme C)

Reaction:

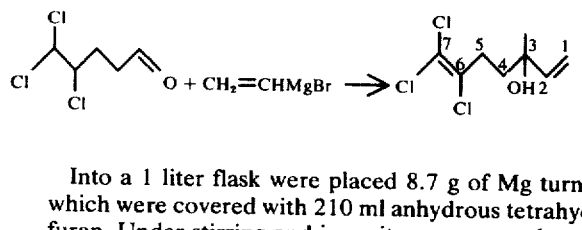

Into a 1 liter flask were placed 8.7 g of Mg turnings which were covered with 210 ml anhydrous tetrahydrofuran. Under stirring and in a nitrogen atmosphere, 30 g of vinyl bromide in 70 ml of tetrahydrofuran were dripped in at a temperature maintained at 40°–50° C. On completion of this addition, the reaction mass was reflux-heated for 30 minutes, cooled to room temperature and into it was dripped a solution of the ketone obtained according to the preceding example (79 g) in tetrahydrofuran. The temperature was maintained at about 30° C.

After resting 12 hours at room temperature, the reaction mixture was hydrolized with ice and ammonium chloride. It was then decanted, the floating raw oil was separated and added to the ether extracts of the aqueous solution.

After drying, the ether extracts left, as residue, a raw oil (93.1g) which was used as such for the subsequent reaction.

Example 56

Preparation of the cis-trans mixture
1,1,2-trichloro-7-bromo-5-methylhept-1,5-diene
(Scheme C) Reaction:

82.7 g of the raw oil obtained according to example 55 were added at 0°–5° C to a solution of 40 g of HBr in 200 ml of icy $CH_3COOH$.

After stirring for 30 minutes at 0° C, the reaction mixture was poured into water and ice, and the organic layer that separated was additioned to the ether extracts of the aqueous phase.

The extracts were washed with an aqueous solution of sodium carbonate and then with water. After drying on $Na_2SO_4$, the ether was evaporated and the raw bromide thus obtained (92.2 g) was used as such in the subsequent reaction.

The M.N.R. spectrum of a sample, purified by preparatory thin-layer gas chromatography, was examined. It was thus possible to observe that the product is a mixture of 1,1,2-dichloro-7-bromo-5-methylhepta-1,5-dienes, consisting for 30% of cis-isomer and for 70% of transisomer.

EXAMPLE 57

Preparation of
1-(6,7,7-trichloro-3-methyl-hepta-2,6-dienyloxy)-3,4methyl endioxybenzene (our mark 5905).

Reaction:

Under stirring, to 66 g of 3,4-methylen-dioxyphenol in 20 ml of diethanol and in an inert atmosphere, there were added 1.7 g of 85% KOH in 30 ml ethanol. The mixture was cooled down to 0° C and to it were added 5.3 g of raw bromide obtained according to example 56.

The reaction mass was stirred for 12 hours at 0° C and then poured into ice. The organic residue that separated and the ether extracts of the aqueous phase were combined and were decolored with active coal and concentrated under reduced pressure. Thereby were obtained 5.1 g of raw 1-(6,7,7-trichloro-3-methyl-hepta-2,6-dienyloxy)-3,4-methylendioxybenzene which was purified by preparatory thin-layer chromatography on silica gel (solvents: n-hexane/ethyl ether 90:10).

Thereby were obtained 2.28 g of a pure product identified on the basis of analysis of its M.N.R. spectrum.

EXAMPLE 58

Biological activity

The tests were carried out in a conditioned environment on the following species of insects: *Tenebrio molitor*, *Pieris brassicae*, *Spodoptera littoralis*, *Anagasta kuemniella*, *Tribolium confusion*, *Aedes aegypti*, *Musca domestica*. The conditions under which the test were conducted are indicated hereunder in the given order, species after species:

1. *Tenebrio m.* — Pupae aged 0-24 hours were treated by topical application on the last but penultimate urosternite with an acetone solution of the product (2 cu.mm).

Appraisal of the results was made after about 9 days when the insects of the test group had completely emerged from the cocoons.

2. *Pieris b.* — The larvae of the last age were treated by topical application on the first urosternites with an acetone solution of the product (2 cu.mm). The appraisal of the results was made about every 5 days until complete emergence from the cocoons of the adults of the test group.

3. *Spodoptera l.* Larvae of the last age were treated by topical treatment of the last urosternites with an acetone solution of the product (2 cu.mm). The results were appraised about every 5 days until the adults of the test group had completely emerged.

4. *Anagasta k.* — 5 grams of maize meal were uniformly treated with an acetone solution of the product. 24 hours after the treatment the meal was infested with 21 day larvae. Appraisal of the results were made every 3–4 days starting from the beginning of the emergence of the adults up to the end of the emergence thereof.

5. *Tribolium c.* — 5 g of wheat meal were uniformly treated with an acetone solution of the product. 24 hours after the treatment the meal was infested with 22 day larvae. Appraisal of the results was made after about 45 days when the insects of the test group had completed their emergence.

6. *Musca d.* — 5 g of sugar and 5 g of a mixture consisting of sugar, milk and egg yolk powder, were treated separately with an acetone solution of the product. After evaporation of the solvent, the sugar and the mixture were separately introduced into two beakers together with 50 adult flies, 25 males and 25 females. Subsequently, the above mentioned egg based mixture which was not treated however with the products under examination was administered to the flies fed with the treated sugar. After the first egg laying, 100 eggs were transferred in pabulum. After 2 days the percentage of hatched eggs was checked; after a further 5 days the pupae were gathered and counted, and after another 4 days the percentage of emerged adults was ascertained.

7. *Aedes aegypty* — 33 cc of an acetone solution of the product were added to 297 cc of spring water into which were successively transferred 25-days larvae supplied with an appropriate nourishment. Appraisal of the result was undertaken every 2–3 days, up to the end of the emergence in the witness group.

Criteria for evaluating the insect activity of tests 1,2,3,4,5,7

The activity index adopted was the percentual ratio of dead individuals and ill-formed and abnormal individuals with respect to the treated individuals, according to the following formula:

$$\text{Activity} = \frac{\text{individuals (dead + ill-formed + abnormal)}}{\text{treated individuals}}$$

Criteria for evaluating the results of the test on the Musca domestica (6).

The activity index adopted was the ratio, in percent, of unhatched eggs against the total of eggs laid by the insects treated, as indicated by the following formula:

$$\text{Activity} = \frac{\text{unhatched eggs}}{\text{total of laid eggs}}$$

| Compound mark No. | Tenebrio molitor γ/insect | | | | Pieris brassicae γ/insect | | Spodoptera littoralis γ/insect | | Aedes aegypti ppm | | | Ephestia kuniella ppm | | Tribolium confusum ppm | | Musca domestica % | | |
|---|---|---|---|---|---|---|---|---|---|---|---|---|---|---|---|---|---|---|
| | 200 | 20 | 2 | 0.2 | 200 | 20 | 200 | 20 | 2 | 0.4 | 0.2 | 2000 | 200 | 2000 | 200 | 20 | 1 | 0.2 |
| 5521 | 100 | 87 | | | 100 | 50 | 60 | 60 | 81 | 22 | | 100 | 74 | 100 | | | | 43 |
| 5522 | 100 | 93 | 95 | | 100 | 37 | 40 | | 100 | 93 | 57 | 100 | 78 | 100 | | | | 60 |
| 5523 | 100 | 77 | | | 20 | | 33 | | 46 | 28 | | 100 | 26 | 100 | | | 93 | |
| 5524 | | | | | 90 | 37 | 67 | | 50 | | | 100 | | | | | 23 | |
| 5525 | | | | | 80 | | 100 | | 25 | | | 100 | 89 | | | | | |
| 5526 | | | | | 40 | | 83 | | 73 | | | 55 | | | | | | |
| 5527 | 100 | 100 | 90 | | 90 | 75 | 50 | | 76 | 42 | | 100 | 33 | 100 | | | 73 | 32 |
| 5528 | | | | | | | 50 | | | | | 95 | | | | | | |
| 5742 | 100 | 100 | 92 | | 87 | 20 | 93 | 20 | 83 | 24 | | 100 | | 100 | | | | |
| 5531 | | | | | | | 33 | | 39 | | | 100 | | | | | | |
| 5621 | 100 | 75 | | | 75 | | | | 71 | | | 100 | 50 | | | | 100 | |
| 5622 (1) | | | | | | | | | 84 | | | | | | | | | |
| 5623 (2) | | | | | | | 75 | | 74 | | | | | | | | | |
| 5624 (3) | | | | | | | 100 | | 42 | | | 100 | 33 | | | | 36 | |
| 5625 (4) | | | | | | | | | 42 | | | 51 | | | | | | |
| 5631 | — | 100 | 95 | 85 | | 60 | 40 | | 39 | | | 100 | 100 | | | | 84 | |
| 5632 | — | 100 | 100 | — | 100 | | | | 100 | 100 | 69 | 100 | 50 | | | | | |
| 5633 | | | | | | 20 | 40 | | | | | 89 | | | | | | |
| 5712 | | | | | 28 | | | | | | | | | | | | | |
| 5714 | | | | | | | 75 | | 100 | 93 | | | | | | | | |
| 5715 | | | | | 100 | | | | 35 | | | | | | | | 27 | |
| 5717 | 86 | | | | 75 | | | | | | | | | | | | 56 | |

(1) 1(7,7-dichloro-3-methyl-hepta-2,2-dienyloxy)-3-methoxy-benzene
(2) 3(7,7-dichloro-3-methyl-hepta-2,6-dienyloxy)methylbenzene
(3) 2,4,6-trichloro-1-(7,7-dichloro-3-methyl-hepta-2,6-dienyloxy)-benzene
(4) 3(7,7-dichloro-3-methyl-hepta-2,6-dienyloxy)-nitrobenzene

| | Tenebrio Molitor pupae γ/ins. | | | | Trieolium Confusum larvae ppm | | | Pieris Brassicae larvae γ/ins. | | |
|---|---|---|---|---|---|---|---|---|---|---|
| | 200 | 20 | 2 | 0.2 | 2000 | 200 | 20 | 200 | 20 | 2 |
| 5738 | 100 | 64 | | | 100 | 44 | | 51 | | |
| 5739 | 100 | 88 | 75 | 33 | 100 | 44 | | 87 | | |
| 5797 | 0 | | | | 21 | | | 16 | | |
| 5905 | 53 | | | | 44 | | | 11 | | |
| 5912 | 78 | 80 | 38 | | 23 | | | | | |
| 5953 | 100 | 75 | | | 100 | 18 | | 80 | | |
| 5977 | 17 | | | | 33 | | | | | |
| 5979 | 100 | | | | 59 | | | | | |
| 5982 | 8 | | | | 61 | | | | | |
| 6062 | 0 | | | | 0 | | | | | |
| 6063 | 4 | | | | 0 | | | | | |
| 6066 | 35 | | | | 10 | | | | | |
| 6133 | 0 | | | | 7 | | | | | |
| 6134 | 0 | | | | 7 | | | | | |
| 6135 | 100 | 30 | | | 100 | 0 | | | | |
| 6136 | 0 | | | | 12 | | | | | |
| 6137 | 0 | | | | 36 | | | | | |
| 6140 | 100 | 30 | | | 100 | 0 | | | | |
| 6288 | 100 | 100 | 96 | 98 | 100 | 100 | 12 | 100 | 100 | 84 |
| 6351 | 100 | 100 | 100 | 50 | 100 | 100 | 6 | 100 | 100 | 0 |

| | Spodoptera Littoralis larvae γ/ins. | | | Anagasta Kuniella larvae ppm | | | Aedes aegypti larvae ppm | | | Musca domestica adults % | | |
|---|---|---|---|---|---|---|---|---|---|---|---|---|
| | 200 | 20 | 2 | 2000 | 200 | 20 | 2 | 0.4 | 0.2 | 1 | 0.2 | 0.05 |
| 5738 | 0 | | | 100 | 95 | | 90 | 43 | | 100 | 68 | |
| 5739 | | | | 94 | | | 100 | 29 | | 100 | 22 | |
| 5797 | 0 | | | 100 | 18 | | 27 | | | insettic. 13 | | |
| 5905 | 20 | | | 100 | 25 | | 100 | 47 | | 69 | | |
| 5912 | 17 | | | 61 | | | 0 | | | 37 | | |
| 5953 | 0 | | | 100 | 5 | | 33 | | | 16 | | |
| 5977 | 20 | | | 100 | 30 | | 0 | | | 6 | | |

-continued

| | | | | | | | | | |
|---|---|---|---|---|---|---|---|---|---|
| 5979 | 20 | | 60 | | | 0 | | 58 | |
| 5982 | 0 | | 30 | | | 12 | | 85 | 34 |
| 6062 | 17 | | 100 | 17 | | 66 | | 45 | |
| 6063 | 33 | | 100 | 28 | | 69 | | 40 | |
| 6066 | 20 | | 39 | | | 81 | | 17 | |
| 6133 | 0 | | 100 | 0 | | 39 | | 50 | |
| 6134 | 0 | | 100 | 0 | | 45 | | 14 | |
| 6135 | 0 | | 94 | 0 | | 59 | | 2 | |
| 6136 | 0 | | 100 | 0 | | 97 | 29 | 2 | |
| 6137 | 16 | | 100 | 12 | | 100 | 38 | 9 | |
| 6140 | 0 | | 100 | 47 | | 20 | | 12 | |
| 6288 | 100 | 100 | 100 | 100 | 100 | 39 | 100 | 100 | 89 | 49 |
| 6351 | 66 | | 100 | 54 | | 18 | | | |

We claim:

1. Compounds characterized in having a high juvenile hormone activity similar to that of the Roller et al. juvenile hormone and selected from the group consisting of 1-(7,7-dichloro-3-methyl-hepta-2,6-dienyloxy)-3,4-methylendioxybenzene; 1-(6,6-dichloro-3-methyl-hexa-2,5-dienyloxy)-3,4-methylendioxybenzene; 1-(9,9-dichloro-3,7-dimethyl-nona-2,6,8-trienyloxy)-3,4-methylenedioxy-benzene; and 1-(6,7,7-trichloro-3-methyl-hepta-2,6-dienyloxy)-3,4-methylenedioxy-benzene.

2. The compound according to claim 1 which is 1-(7,7-dichloro-3-methyl-hepta-2,6-dienyloxy)-3,4-methylendioxybenzene of the formula:

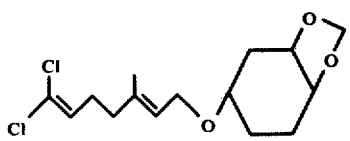

3. The compound according to claim 1 which is 1-(6,6-dichloro-3-methyl-hexa-2,5-dienyloxy)-3,4-methylendioxybenzene of the formula:

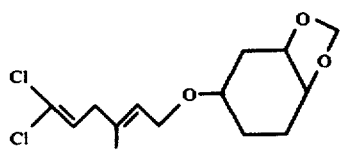

4. The compound according to claim 1 which is 1-(9,9-dichloro-3,7-dimethyl-nona-2,6,8-trienyloxy)-3,4-methylendioxybenzene of the formula:

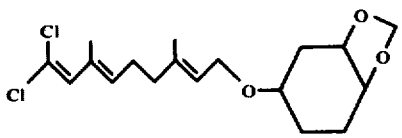

5. The compound according to claim 1 which is 1-(6,7,7-trichloro-3-methyl-hepta-2,6-dienyloxy)-3,4-methylendioxybenzene of the formula:

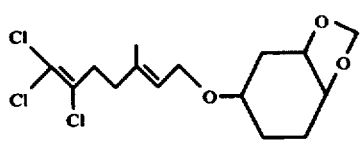

6. Insecticidal compositions the essential constituent is an insecticidally effective amount of a compound according to claim 1 and further characterized in that they exhibit an activity against insects similar to that of the Roller et al. juvenile hormone.

7. The method of combatting infestation by harmful insects which consists in development of such insects from the larval stage to the adult stage thereof is inhibited by spreading on the natural habitat of the adult insect, and/or on the food of the adult insect, and/or on the pupae or larval and/or on the habitat of the pupae and larval, and/or on the food of the pupae and larval, a composition the essential constituent of which is an insecticidally effective amount of a compound according to claim 1 in an amount greater than 0.1 ppm per insect.

* * * * *

UNITED STATES PATENT AND TRADEMARK OFFICE
CERTIFICATE OF CORRECTION

PATENT NO. : 4,000,312
DATED : December 28, 1976
INVENTOR(S) : Paolo PICCARDI et al It is certified that error appears in the above-identified patent and that said Letters Patent are hereby corrected as shown below:

[75] The assignee should be --Montedison S.p.A., Milan, Italy--

Col. 1, line 10, "Anderwandte" should be --Angewandte--

Col. 1, line 34, before "dichloro-", the word "had" should be --has--

Col. 3, in (2) Scheme B, the formula

"$(B_2)$ mixture $\begin{cases} CCl_3-CH=CHR^1 \\ CCl-CH-CHR^1Cl \end{cases}$" should be --$(B_2)$ mixture $\begin{cases} CCl_3-CH=CHR^1 \\ CCl_2=CH-CHR^1Cl \end{cases}$-- and "$(B_3)$ $CCl_3C=CH-CHR'-CHR-COR^3$" should be --$(B_3) CCl_3-CH_2-CH=CR^1-CHR^2-COR^3$ --.

Col. 7, line 44, The language "obtained by; or, by hydrogenation" should be --obtained; or, by hydrogenation - --.

UNITED STATES PATENT OFFICE
CERTIFICATE OF CORRECTION

Patent No. 4,000,312  Dated December 28, 1976

Inventor(s) Paolo PICCARDI et al

It is certified that error appears in the above-identified patent and that said Letters Patent are hereby corrected as shown below:

<u>Col. 12</u>, in Item (20)  "4-(6,6-dichloro-3-methyl-2,5-hexandienyloxy)" should be - - -

4-(6,6-dichloro-3-methyl-2,5-hexadienyloxy) - - -.

<u>Col. 16</u>, line 6 of Example 1, "where" should be - - - were - - -.

<u>Col. 16</u>, line 7 of Example 1, "KOH ml of ethyl-cellosolve" should be - - - KOH in 500 ml of ethyl-cellosolve - - -.

<u>Col. 16</u>, line 8 of Example 2, the formula "$CCl_2:CH_2Cl$" should be - - - $CCl_2:CH.CH_2Cl$ - - -.

<u>Col. 16</u>, line 8 of Example 3, "100 of ethyl ether" should be - - - 100 ml of ethyl ether - - -.

<u>Col. 17</u>, line 3 of Example 4, "80 of anhydrous tetrafuran" should be - - - 80 ml of anhydrous tetrafuran - - -.

<u>Col. 17</u>, line 5 of Example 4, "additional" should be - - - additioned - - -.

UNITED STATES PATENT OFFICE
CERTIFICATE OF CORRECTION

Patent No. 4,000,312    Dated December 28, 1976

Inventor(s)    Paolo PICCARDI et al

It is certified that error appears in the above-identified patent and that said Letters Patent are hereby corrected as shown below:

Col. 17, line 6 of Example 4,    "70" should be - - - 70 ml - - -.

Col. 17, last line of Example 4,    "68° - 72°c" should be - - - 68° - 72°C - - -.

Col. 18, line 3 of Example 24,    "pentanote" should be - - - pentanoate - - -.

Col. 19, lines 4 and 5 of Example 27.

"1,1-dichloro-7-dichloro-7-bromo-5-ethyl-1,5-heptadiene" should be - - - 1,1-dichloro-7-bromo-5-ethyl-1,5-heptadiene - - -.

Col. 20, line 8 of Example 39,    "wad" should be - - - was - - -.

Col. 21, last line,    "mixtures" should be - - - mixture - - -.

Col. 22, line 11,    "254-days" should be - - - 25 4-days - - -.

UNITED STATES PATENT OFFICE
CERTIFICATE OF CORRECTION

Patent No. 4,000,312     Dated December 28, 1976

Inventor(s) Paolo PICCARDI et al

It is certified that error appears in the above-identified patent and that said Letters Patent are hereby corrected as shown below:

Col. 24, line 4,    after "dried" the word "or" should be - - - on - - -.

Col. 24, line 8,    "0.1 Hg" should be - - - 0.1 mm Hg - - -.

Col. 24, line 15 of Example 48,    "dired" should be - - - - - - dried - - -.

Signed and Sealed this

Twenty-fifth Day of September 1979

[SEAL]

Attest:

Attesting Officer

LUTRELLE F. PARKER
*Acting Commissioner of Patents and Trademarks*

UNITED STATES PATENT OFFICE
CERTIFICATE OF CORRECTION

Patent No. 4,000,312     Dated December 28, 1976

Inventor(s) Paolo PICCARDI et al

It is certified that error appears in the above-identified patent and that said Letters Patent are hereby corrected as shown below:

Col. 3, in (2) Scheme A, the formula

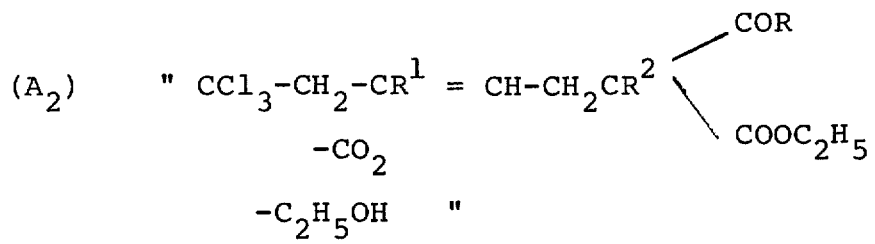

should be -

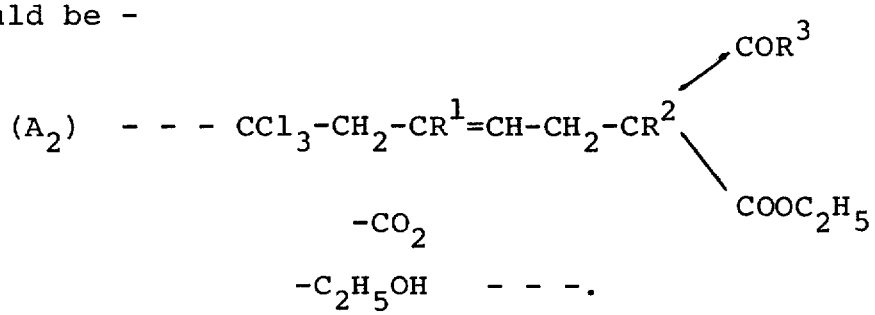

UNITED STATES PATENT OFFICE
CERTIFICATE OF CORRECTION

Patent No. 4,000,312     Dated December 28, 1976

Inventor(s) Paolo PICCARDI et al

It is certified that error appears in the above-identified patent and that said Letters Patent are hereby corrected as shown below:

Col. 3, in Scheme (B) the formula ($B_2$) mixture
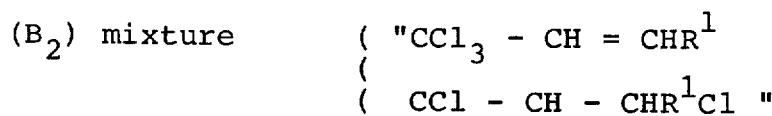

should be:

($B_2$) mixture
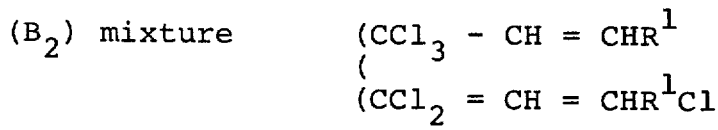

Col. 3, in Scheme (B)    the formula as shown in the Certificate Of Correction dated September 25, 1979 is incorrect and should read —

($B_3$)      $CCl_2 = CHR^1-CHR^2-COR^3$.

UNITED STATES PATENT OFFICE
CERTIFICATE OF CORRECTION

Patent No. 4,000,312     Dated December 28, 1976

Inventor(s) Paolo PICCARDI et al

It is certified that error appears in the above-identified patent and that said Letters Patent are hereby corrected as shown below:

<u>Col. 5, in Scheme C,</u> the formula ($C_2$)    " $A-CR^3=CR^4-CHR^5Br$

2 H    "

should be ($C_2$)    - - - $A-CR^3=CR^4-CHR^5Br$

ZH    - - -.

Signed and Sealed this

Ninth Day of December 1980

[SEAL]

Attest:

SIDNEY A. DIAMOND

Attesting Officer     Commissioner of Patents and Trademarks

UNITED STATES PATENT AND TRADEMARK OFFICE
CERTIFICATE OF CORRECTION

PATENT NO. : 4,000,312
DATED : December 28, 1976
INVENTOR(S) : Paolo PICCARDI et al It is certified that error appears in the above—identified patent and that said Letters Patent is hereby corrected as shown below:

Col. 3, in Scheme (B) the formula $(B_2)$ mixture  $(CCl_3 - CH = CHR^1$ $(CCl_2 = CH = CHR^1Cl$ should be $(B_2)$ mixture  $(CCl_3 - CH = CHR^1$ $(CCl_2 = CH - CHR^1Cl$ Col. 3, in Scheme (B) the formula $(B_3)$ mixture  $(CCl_3-CH_2-CH=CR^1-CHR^2-COR^3$ should be $(B_3)$ mixture  $(CCl_2=CH-CHR^1-CHR^2-COR^3$ Signed and Sealed this Tenth Day of March 1981

[SEAL]

Attest:

RENE D. TEGTMEYER

Attesting Officer    Acting Commissioner of Patents and Trademarks